United States Patent [19]

Owens

[11] 4,025,964
[45] May 31, 1977

[54] MAGNETIC ELECTRICAL CONNECTORS FOR BIOMEDICAL PERCUTANEOUS IMPLANTS

[75] Inventor: Lester J. Owens, Titusville, Fla.

[73] Assignee: The United States of America as represented by the Administrator of the National Aeronautics and Space Administration, Washington, D.C.

[22] Filed: July 30, 1976

[21] Appl. No.: 709,849

[52] U.S. Cl. .................................. 3/1; 128/1 R; 339/12 R
[51] Int. Cl.² .......................................... A61F 1/00
[58] Field of Search ............ 339/12 R, 12 G, 12 L, 339/12 S, 27, 46, 48, 47 R, 47 C, 65, 64 R, 64 M, 222, 126 R, 126 J; 128/1 R; 3/1

[56] References Cited
UNITED STATES PATENTS

| | | | |
|---|---|---|---|
| 3,521,216 | 7/1970 | Tolegian | 339/12 R |
| 3,663,965 | 5/1972 | Lee, Jr. et al. | 3/1 |
| 3,808,577 | 4/1974 | Mathauser | 339/12 R |
| 3,810,258 | 5/1974 | Mathauser | 339/12 R |
| 3,952,726 | 4/1976 | Hennig et al. | 128/1 R |

Primary Examiner—Roy Lake
Assistant Examiner—DeWalden W. Jones

Attorney, Agent, or Firm—James O. Harrell; John R. Manning

[57] ABSTRACT

A biomedical percutaneous connector for providing electrical connection between electrical conductors carried externally of a patient's body and electrical conductors implanted within the body of the patient. The connector includes a socket having an enlarged disk shaped base portion for being implanted below the patient's skin. A cylindrical portion is integral with the base portion and extends outwardly of the skin. A conical recess is provided in an upper end of the cylindrical portion and has a magnet located in the base thereof. Inclined conductive strips are carried on an upper end of the cylindrical portion adjacent the conical recess to which electrical conductors are attached and extend into the patient's body. A complementary shaped plug which also has electrical contacts provided thereon is adapted to fit within the conical recess of the socket. Guide grooves and protrusions are provided on the socket and plug for aiding in positioning the plug relative to the socket. The plug is held in the socket by the magnetic force between the magnet located in the base of the cylindrical portion and magnetic material provided in the plug.

6 Claims, 1 Drawing Figure

U.S. Patent    May 31, 1977    4,025,964
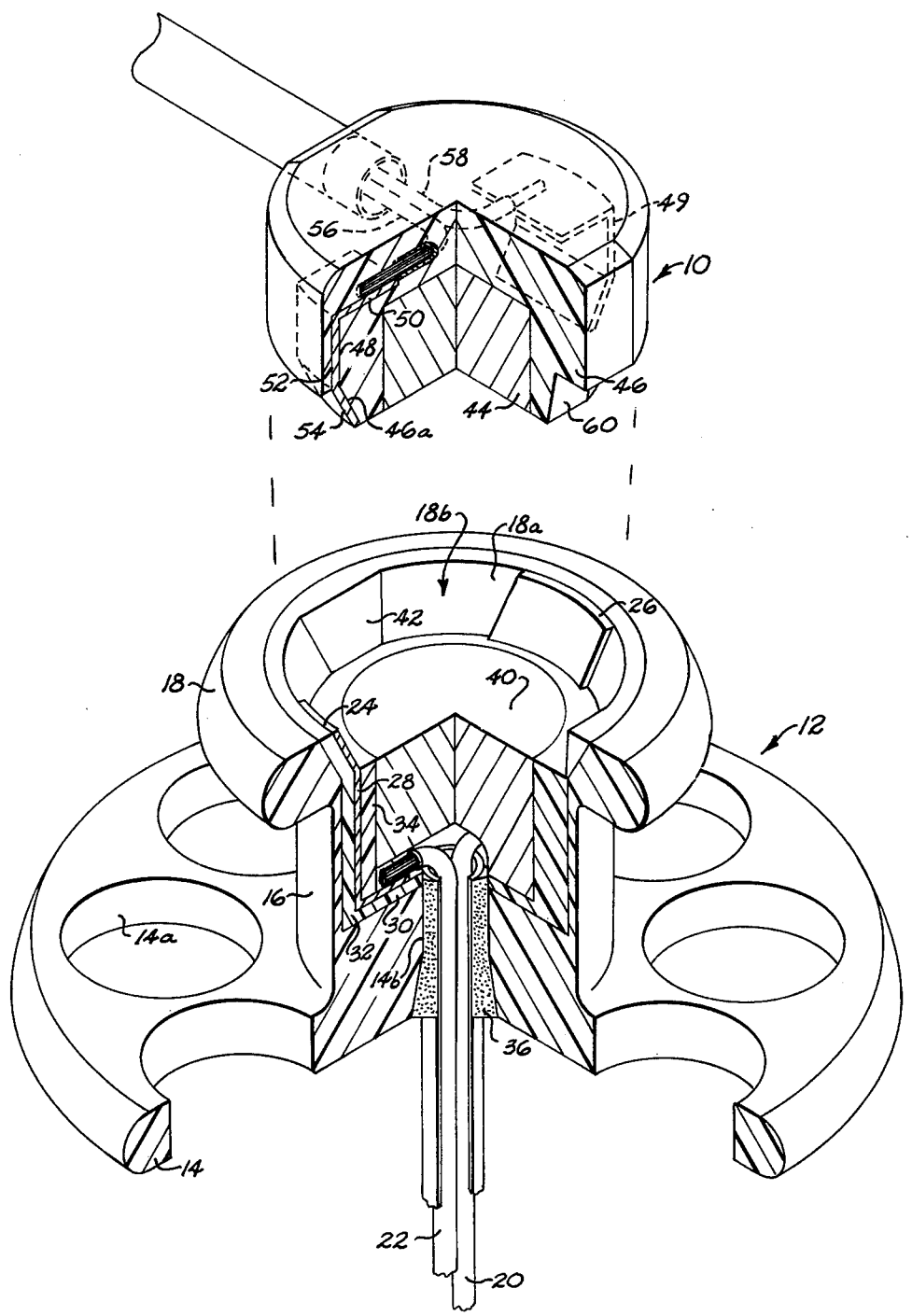

MAGNETIC ELECTRICAL CONNECTORS FOR BIOMEDICAL PERCUTANEOUS IMPLANTS

ORIGIN OF THE INVENTION

The invention described herein was made by an employee of the United States Government and may be manufactured and used by or for the Government for governmental purposes without payment of any royalties thereon or therefor.

BACKGROUND OF THE INVENTION

The present invention relates to an electrical biomedical percutaneous connector and more particularly to a connector which includes a socket and plug which can be readily connected and disconnected.

Electrical plugs and biomedical percutaneous implants are well known; however, one problem with such devices is to provide an implanted connector which can be readily connected and disconnected. The various percutaneous implants which have been developed in the past normally protrude beyond the skin of the patient. These protrusions created a problem in that they have a tendency to snag on clothing and bedding. Another difficulty with percutaneous implants heretofore developed was in maintaining such in satisfactory hygenic conditions.

One particular bacteria-resistance percutaneous conduit device is disclosed in U.S. Pat. No. 3,663,965. While this device facilitates passage of wires and tubes through the external epidermis in a hygenic manner, there is no means of connecting and disconnecting the wires therefrom.

Magnetic plugs and socket assemblies such as disclosed in U.S. Pat. Nos. 3,521,216 and 3,810,258 are well known, however, there is no showing in any of these references of a bacteria-resistant plug and socket assembly which can be readily implanted below the skin of a patient while permitting quick connection and disconnection.

SUMMARY OF THE INVENTION

This invention relates to a biomedical percutaneous connector for providing electrical connection between electrical conduits carried externally of the body and electrical conduits implanted within the body of a patient. The connector includes a socket having an enlarged disk shaped base portion for being implanted below the skin of a patient. A cylindrical portion integral with the base member extends outwardly therefrom and passes through the skin of the patient. A conical recess is provided in an upper end of the cylindrical portion and has a magnet carried adjacent the base thereof. Inclined conductive strips are carried in an upper end of said cylindrical portion adjacent the conical recess. Electrical conductors are connected to the conductive strips and extend through the cylindrical portion and said base portion.

A non-conductive plug which is complementary in shape to the conical recess is provided for being inserted into the socket. The plug includes an inclined wall provided adjacent a bottom portion of a non-conductive body which has inclined electrically conductive elements thereon that mate with the inclined conductive strips carried within the recess so that when the plug is inserted in the socket, a sure and certain electrical connection is provided therebetween. Electrical conductors are connected to the conductive elements of the plug and extend through the non-conductive body.

A magnetic material is carried adjacent the bottom portion of the non-conductive body of the plug so that as the plug is inserted within the socket, the magnetic force between the magnetic material and the magnet holds the plug in the socket.

The socket and the plug also have cooperating guide slots and protrusions so as to prevent the plug from rotating within the socket once inserted therein and for also aiding in properly placing the plug within the socket.

Accordingly, it is an important object of the present invention to provide a percutaneous implant which is relatively safe in that it can be disconnected readily without damaging the implanted female socket.

Still another important object of the present invention is to provide an implanted connector which minimizes accidental tearing of the implant from the patient's skin.

Still another important object of the present invention is to provide a biomedical percutaneous connector which includes a socket that can be readily cleaned.

Still another important object of the present invention is to insure a certain and repeatable force on each set of electrical contacts as the result of the wedging action of the conical interface between the electrical contacts and the magnetic attraction between the connector socket and plug.

Still another important object of the present invention is to provide a percutaneous implant which remains relatively flush with the surface of the skin so as to minimize the chance of such snagging on clothing or bedding.

These and other objects and advantages of the invention will become apparent upon reference to the following specification, attendant claims, and drawing.

BRIEF DESCRIPTION OF THE DRAWING

The Figure on the drawing is an enlarged perspective view, partially in section illustrating a biomedical percutaneous connector constructed in accordance with the present invention.

DESCRIPTION OF A PREFERRED EMBODIMENT

Referring in more detail to the drawing, there is illustrated a biomedical percutaneous connector constructed in accordance with the present invention.

The biomedical percutaneous connector consists of a pair of mating connector elements which include a male plug generally designated by the reference character 10 and a female socket generally designated by the reference character 12. In normal uses, the female socket is implanted in a patient with a lower portion thereof extending below the skin of the patient. It is to be understood that when reference is made to the socket portion extending outwardly beyond the skin of the patient, after the skin grows up around a central portion of the socket, the skin is normally level with the lower edge of the rim of the cylindrical portion to be described in more detail hereinafter.

The socket 12 may be constructed of any suitable biocompatible material such as biocompatible vitreous carbon material.

The socket includes an enlarged disk shaped member 14 which is normally implanted below the skin of the patient. Integral with the disk shaped portion 14 and extending upwardly therefrom is a hollow, cylindrical portion 16 which has an axial bore extending therethrough. Integral with an upper end of the cylindrical portion 16 is a rim 18. The rim 18 has an inner conical wall surface 18a which forms a conical recess 18b in the outer end of the cylindrical portion 16. This conical recess 18b is shallow and exposed; therefore, it can be readily cleaned with a cotton pad or the like.

The socket includes electrical conductors 20 and 22 which provide an electrical path to various members such as nerves or muscles within the patient's body. These electrical conductors are, in turn, attached to lower ends of electrically conductive foil or strip contact members 24 and 26. These foil members 24 and 26 may be solid gold or gold plated where such is desirable for certain applications.

The electrical conductive foil members 24 and 26 include an inclined upper portion which has a vertically extending intermediate portion 28 integral therewith which terminates in a horizontally extending leg 30. Each of the foil members 24 and 26 are shaped in the same manner. However, only one of such is illustrated in detail for purposes of clarity. The foil members 24 and 26 are sandwiched between insulating plastic layers 32 and 34 which are utilized for holding them within the axial bore of the cylindrical portion 16. As noted, the electrical conductors 22 and 20 are welded or connected by any suitable means to the horizontal portion 30 of a respective foil member 24 or 26. The electrical conductors 22 and 20 extend through a bore 14b provided within the lower end of cylindrical portion 16 for communication therewith and is sealed with any suitable biocompatible plastic 36 so that fluids from the patient's body will not penetrate upwards into the socket.

A cylindrical shaped magnet 40 is carried within the axial bore of the cylindrical portion 16 with the wall thereof being flush against the insulating plastic or epoxy layer 34. An upper surface of the magnet 40 is planar and terminates substantially at the junction between the inclined portions of the foil strips 24 and 26 and the vertically extending portions 28. All voids within the axial bore of the cylindrical portion 16 from the top of the magnet 40 to the base plane are filled with insulating plastic.

Wedge shaped guide protrusions 42 are provided on the inner conical wall surface 18a of the conical recess 18b which, in turn, cooperates with complementary wedge shaped slots formed in a lower surface of the plug 10.

Referring now to the plug 10, such consists of an inner cylindrical magnetic material 44 which has an insulating plastic body 46 molded thereon. Positioned in the insulating plastic body 46 are a pair of foil or strip contacts 48 and 49, each of which includes an upper horizontal portion 50, a vertically extending portion 52 and an inclined lower portion 54. Electrical conductors 56 and 58 are attached to the foil or strip contacts 48 and 49 respectively. The entire plug is enclosed within a plastic potting compound and is substantially cylindrical in shape. As can be seen in the drawing, the plastic potting compounds form a solid integral unit.

The lower portion of the plug 10 has an inclined wall surface 46a which is conical so as to conform to the complementary inner wall surface 18a of the plug 12. The inclined lower portions 54 of the contacts 48 and 49 lay against the inclined wall surface 46a. The angles of the inner conical wall surface 18a and inclined wall surface 46a are such that when the plug 10 is inserted in the socket 12, the magnetic material 44 is prevented from touching the magnet 40 and thereby causes the foil contacts 48 and 49 of plug 10 to be wedged into engagement with the foil contacts 24 and 26 of socket 12. This particular construction insures that there is always a positive contact between the foil contacts 24 and 26 of the socket 12 and 48 and 49 of the plug 10 even when the contacts become worn or when there is a slight misalignment therebetween. It is to be understood, of course, that instead of using a single magnet 40 and magnetic material 44, two magnets of opposite polarity could be used or a magnet could be placed in the plug 10 and magnetic material in the socket 12. The primary purpose of the magnets is to provide a magnetic force of a predetermined value for holding the plug within the socket.

The inclined wall surface 46a is provided with one or more wedge shaped slots 60 into which the inclined wedge shaped protrusions 42 extend when the plug 10 is inserted in the socket 12. These protrusions 42 and slots 60 serve as a combined key and guide means for positioning the foil contacts 24, 26, 48 and 49 in proper wedging engagement and for preventing the plug 10 from rotating in the socket 12.

The wedge shaped slot 42 and the wedge shaped protrusion 60 should be machined flat enough so that there is no locking force therebetween. This allows the foil contacts 24, 26, 48 and 40 to readily separate and prevents accidental tearing of the socket 12 out of the patient's body if the plug or conductors connected thereto are accidentally pulled upon. Other types of key and guide members may be used to position the plug 10 and prevent it from rotating in the socket 12. For example, the protrusion 42 and slot 60 could be reversed on the plug 10 and socket 12. The key and guide members may also be positioned in any convenient manner and be of any size or shape.

While FIG. 1 merely discloses a bipolar connector, it is to be understood that a tripolar connector could be manufactured in the same manner with the exception that instead of using two foil contacts as illustrated, three foil contacts are placed on both the plug 10 and the socket 12 for providing electrical connection between three electrical conductors. Normally, if three foil members are used, they are equally spaced within the socket 12. The disk shaped portion 14 of socket 12 may be solid or provided with spaced openings 14a to seat the socket on the flesh beneath the skin of the patient.

While a preferred embodiment of the invention has been described using specific terms, such description is for illustrative purposes only, and it is to be understood that changes and variations may be made without departing from the spirit or scope of the following claims.

What is claimed is:

1. A biomedical percutaneous connector for providing electrical connection between electrical conductors located externally of a patient's body and electrical conductors implanted underneath the patient's skin, said connector comprising:
    a. pair of mating connector elements;
    b. a magnet carried within one of said mating connector elements;
    c. magnetic material carried within the other of said mating connector elements;
    d. one of said mating connector elements being a female socket including:

i. a hollow portion having an outer end portion thereof adapted to be extended outwardly through said patient's skin;
ii. an inclined inner wall surface provided on said outer end portion to form a conical recess within said hollow portion;
iii. inclined electrically conductive contacts positioned adjacent said inclined inner wall surface and connected to said electrical conductors implanted underneath said patient's skin;
e. the other end of said mating connector elements being a male plug including:
i. a non-conductive body having an inclined outer wall surface complementary in shape to said conical recess within said female socket;
ii. inclined electrically conductive contacts carried on said inclined outer wall surface and connected to said electrical conductors located externally of said patient's body;
f. whereby when said male plug is inserted in said conical recess of said female socket, said inclined electrically conductive contacts thereof are held in wedging engagement with each other by the magnetic force between said magnet and said magnetic material.

2. The biomedical percutaneous connector as set forth in claim 1 wherein said inclined electrically conductive contacts on said female socket and said male plug are inclined at an angle so that when said male plug is inserted in said female socket, the wedging engagement of said inclined electrically conductive contacts causes said magnet to be slightly spaced from said magnetic material.

3. The biomedical percutaneous connector as defined in claim 1 wherein said female socket further includes:
a. an enlarged disk shaped base portion for being implanted underneath said patient's skin;
b. said hollow portion being cylindrical in shape and formed integral with said enlarged disk shaped base portion;
c. a bore extending through said enlarged disk shaped base portion and communicating with said hollow portion, and
d. said electrical conductors extending through said bore with the ends thereof attached to said inclined electrically conductive contacts of said female socket.

4. The biomedical percutaneous connector as set forth in claim 1 wherein said female socket is constructed of a bio-compatible vitreous carbon material.

5. The biomedical percutaneous connector as set forth in claim 1 wherein said female socket and said male plug are provided with a combined guide and key means to guide said inclined electrically conductive contacts thereof into engagement and to prevent said male plug from rotating with respect to said female socket.

6. The biomedical percutaneous connector as set forth in claim 5, wherein said combined guide and key means comprises:
a. a protrusion carried on said inclined inner wall surface of said female socket; and
b. a slot formed in said inclined outer wall surface of said male plug.

* * * * *